United States Patent [19]

Rosen et al.

[11] Patent Number: 4,962,112
[45] Date of Patent: Oct. 9, 1990

[54] 7-(2-METHYL-4-AMINOPYRROLIDINYL)-NAPHTHRYIDINE AND QUINOLINE COMPOUNDS

[75] Inventors: Terry J. Rosen, Deerfield; Daniel T. Chu, Vernon Hills, both of Ill.

[73] Assignee: Abbott Laboratories, Abbott Park, Ill.

[21] Appl. No.: 160,950

[22] Filed: Feb. 26, 1988

Related U.S. Application Data

[63] Continuation of Ser. No. 81,416, Aug. 4, 1987, abandoned, which is a continuation-in-part of Ser. No. 784,421, Oct. 4, 1985, Pat. No. 4,730,000, which is a continuation of Ser. No. 597,854, Apr. 9, 1984, abandoned, which is a continuation-in-part of Ser. No. 574,227, Jan. 26, 1984, abandoned, which is a continuation-in-part of Ser. No. 514,716, Jul. 18, 1983, abandoned.

[51] Int. Cl.$^5$ .................. A61K 31/40; A61K 31/495; C07D 401/14
[52] U.S. Cl. .................. 514/300; 514/309; 546/123; 546/156
[58] Field of Search ............... 546/123, 156; 514/300, 514/309

[56] References Cited

U.S. PATENT DOCUMENTS 4,616,019 10/1986 Chu, I .
4,730,000 3/1988 Chu, I ................................ 514/254

FOREIGN PATENT DOCUMENTS

EP0131839 1/1985 European Pat. Off. .

Primary Examiner—Richard L. Raymond
Assistant Examiner—James H. Turnipseed
Attorney, Agent, or Firm—Steven F. Weinstock; Steven R. Crowley

[57] ABSTRACT

Naphthyridine and quinoline compounds having the formula:

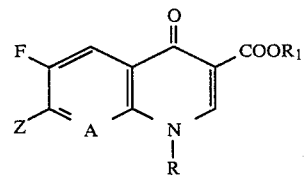

wherein A is CH or N; Z is an amine having the formula:

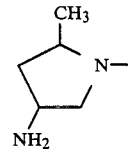

R is o,p-difluorophenyl or p-fluorophenyl; and $R_1$ is hydrogen or a carboxy protecting group. The compounds of the invention have antibacterial activity and improved solubility and pharmacokinetic properties.

13 Claims, No Drawings

7-(2-METHYL-4-AMINOPYRROLIDINYL)NAPH-THRYIDINE AND QUINOLINE COMPOUNDS

This is a continuation of application Ser. No. 081,416, filed Aug. 4, 1987.

This is a continuation-in-part of copending U.S. patent application, Ser. No. 784,421, filed Oct. 4, 1985, which is a continuation of Ser. No. 597,854 filed Apr. 9, 1984, which is a continuation-in-part of Ser. No. 574,227, filed Jan. 26, 1984, which is a continuation-in-part of Ser. No. 514,716, filed July 18, 1983.

This invention relates to new naphthyridine and quinoline derivatives having antibacterial properties, compositions containing the new naphthyridine and quinoline derivatives and methods of treating mammalian patients with the new naphthyridine and quinoline derivatives.

It is known that certain naphthyridine and quinoline compounds exhibit antibacterial properties, notably certain 7-piperazinyl-4-oxo-1,8-naphthyridine-3-carboxylic acids. In European Patent No. 9,425, there are disclosed certain 7-piperazinyl-6-fluoro-1, 4-dihyro-4-oxo-l,8-naphthyridine-3-carboxylic acid derivatives which are substituted in the 1 position with an alkyl or vinyl substituent.

This invention relates to novel antibacterial agents and, more particularly, to 7-substituted 6-fluoro-l,4-dihydro-4-oxo-l,8-naphthyridine and quinoline-3-carboxylic acids and derivatives thereof having the formula:

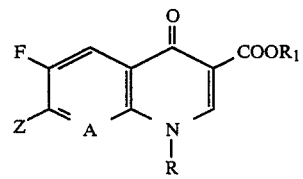

(I)

wherein A is CH or N, R is p-fluorophenyl (1) or o,p-difluorophenyl, R is hydrogen or a carboxy-protecting group and Z is the structure having the formula:

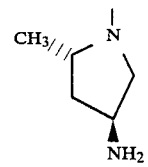

The compounds of this invention have substantially improved solubility properties relative to those lackinq the 2-substituent on the pyrrolidine ring (Table 3); however they still maintain extremely potent antibacterial activity (Tables 1 and 2). The improvement in solubility treatly reduces the probability of crystalluria that is associated with compounds possessing low solubility at physiological pH. The increased solubility also eases in the preparation of i.v. formulations of these drugs. The improved solubility properties of these agents have also resulted in greatly improved oral absorption and pharmacokinetic properties (Table 4).

As used herein, the term "carboxy-protecting group" refers to and includes the residue of a carboxylic acid ester group. Such carboxy-protecting groups are well known to those skilled in the art, having been extensively used in the protection of carboxyl groups in the penicillin and cephalosporin fields, as described in U.S. Pat. Nos. 3,840,556 and 3,719,667, the disclosures of which are incorporated herein by reference. In general, such carboxy-protecting groups can be relatively easily cleaved to yield the corresponding free carboxy group. Representative protecting groups include C to C8 alkyl (e.g., methyl, ethyl, tertiary butyl), benzyl and substituted derivatives thereof such as alkoxy and nitrotrobenzyl groups; also suitable are acyloxyalkyl groups such as a pivaloyloxymethyl group.

The preferred compounds of the invention are those having the formula:

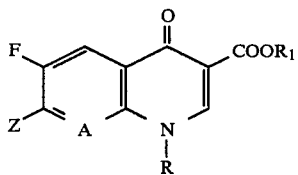

wherein R is as described above and is preferably o,p-difluorophenyl, $R_1$ is as described above and is preferably hydrogen, A is as described above and Z is as described above preferably having the formula:

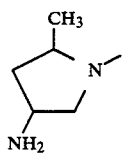

wherein the absolute stereoconfiguration of the 2-methyl substituent is S and the absolute stereoconfiguration of the 4-amino substituent is S.

Also included within the scope of the present invention are pharmaceutically acceptable salts of the foregoing compounds. As used herein, the term "pharmaceutically acceptable salts" refers to non-toxic acid addition salts and alkaline earth metal salts of the compounds of formula 1. The salts can be prepared in situ during the final isolation and purification of the compounds of formula 1, or separately by reacting the free base or acid functions with a suitable organic acid or base. Representative acid addition salts include the hydrochloride, hydrobromide, sulphate, bisulphate, acetate, oxalate, valerate, oleate, palmitate, stearate, laurate, borate, benzoate, lactate, phosphate, tosylate, mesylate, citrate, maleate, fumarate, succinate, tartrate, glucoheptonate, lactobionate, lauryl sulfate salts and the like. Representative alkali or alkaline earth metal salts include the sodium, calcium, potassium and magnesium salts, etc.

It has been found that the compounds of the present invention possess antibacterial activity against a wide spectrum of gram positive and gram negative bacteria, as well as enterobacteria and anaerobes. The compounds of the invention are therefore useful in the antibiotic treatment of susceptible bacterial infections in both humans and animals. In addition, the compounds, by reason of their in vitro activity, may be used in scrub solutions for surface inhibition of bacterial growth.

Susceptible organisms generally include those gram positive and gram negative, aerobic and anaerobic organisms whose growth can be inhibited by the compounds of the invention such as *Staphylococcus, Lactoba-* cillus, Streptococcus, Sarcina, Escherichia, Enterobacter, Klebsiella, Pseudomonas, Acinetobacter, Proteus, . Campylobacter, Citrobacter, Nisseria, Baccillus, Bacteroides, Peptococcus, Clostridium, Salmonella, Shigella, Serratia, Haemophilus, Brucella and other organisms. In addition to exhibiting highly effective antibacterial activity, the compounds of the invention exhibit increased and improved solubility characteristics and oral absorption properties as compared with prior art naphthyridine-3-carboxylic acid compounds.

The compounds of formula 1 may also be formulated into compositions together with pharmaceutically acceptable carriers for parenteral injection, for oral administration in solid or liquid form, for rectal administration, and the like.

Compositions according to the invention for parenteral injection may comprise pharmaceutically acceptable sterile aqueous or nonaqueous solutions, suspensions or emulsions. Examples of suitable nonaqueous carriers, diluents, solvents or vehicles include propylene qlycol, polyethylene glycol, veqetable oils, such as olive oil, and injectable organic esters such as ethyl oleate. Such compositions may also contain adjuvants such as preserving, wetting, emulsifying, and dispersing agents. They may be sterilized, for example, by filtration through a bacteria-retaining filter, or by incorporating sterilizing agents into the compositions. They can also be manufactured in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixers containing inert diluents commonly used in the art, such as water. Besides such inert diluents, compositions can also include adjuvants, such as wetting agents, emulsifying and suspending agents, and sweetening, flavoring and perfuming agents.

Compositions for rectal administration are preferably suppositories which may contain, in addition to the active substance, excipients such as coco butter or a suppository wax.

Actual dosage levels of active ingredient in the compositions of the invention may be varied so as to obtain an amount of active ingredient effective to achieve antibacterial activity in accordance with the desired method of administration. The selected dosage level therefore depends upon the nature of the active compound administered, the route of administration, the desired duration of treatment and other factors. Generally, daily dosage levels of the compounds of Formula 1 of about 0.1 to about 750, more preferably about 0.25 to about 500 and most preferably about 0.5 to about 300 mg. of active ingredient pr kg. of body weight are effective when administered orally to a mammalian patient suffering from an infection caused by a susceptible organism. If desired, the daily dose may be divided into multiple doses for administration, e.g., two or four times per day.

The naphthyridine compounds according to this invention can be prepared by the reaction sequence illustrated below:

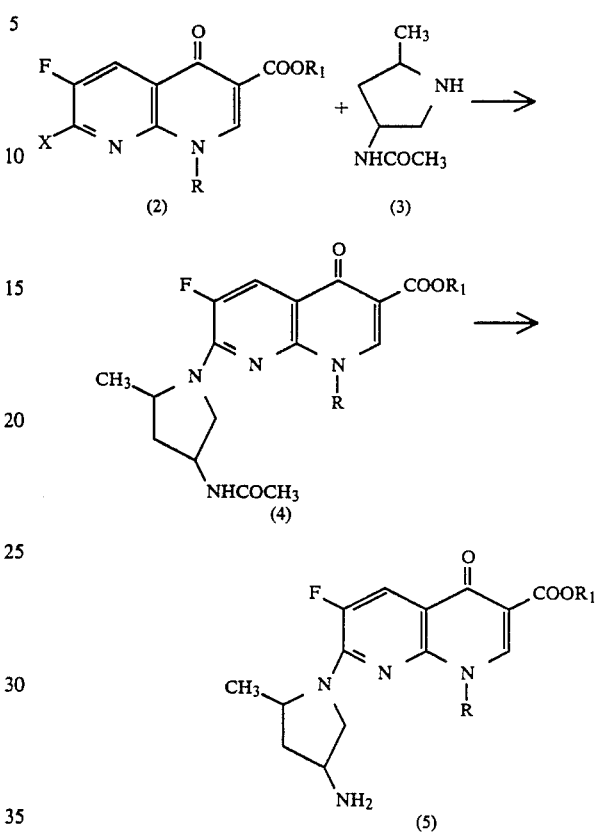

wherein X is a halogen, mesylate or methoxy group and R and $R_1$ are the same as described above.

Heating a compound of the formula (2) with an amine of formula (3) at a temperature of from 20° C. to 150° C., in the presence of a suitable organic polar or non-polar solvent such as dimethylsulfoxide, sulfolane, dimethylformamide (DMF), dimethylacetamide, 1-methy-2-pyrrolidinone, pyridine, water, tetrahydrofuran (THF) or methylene chloride provides compound (4). It is desirable to carry out the reaction in the presence of an acid acceptor such as triethylamine, potassium carbonate or the like at a molar ratio of 1.0 to 2.0 moles of the acid-acceptor per mole of the compound of the formula (2). The amine (3) can also be used as acid acceptor in which 2 or more molar excess of this reagent is used. The ester in (4) is hydrolyzed by treatment with dilute sodium hydroxide in aqueous THF. Subsequent hydrolysis of the N-acetyl group with hydrochloric acid furnishes the naphthyridine (5) ($R_1$=H). The compounds of the formula (2) may be prepared in accordance with the prior art (U.S. Pat. No. 4,616,019).

Amines of the formula (3) may be prepared in accordance with the following reaction scheme.

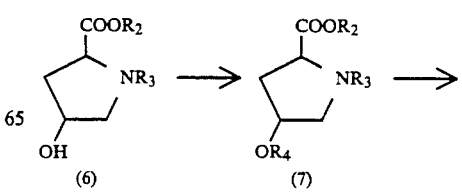

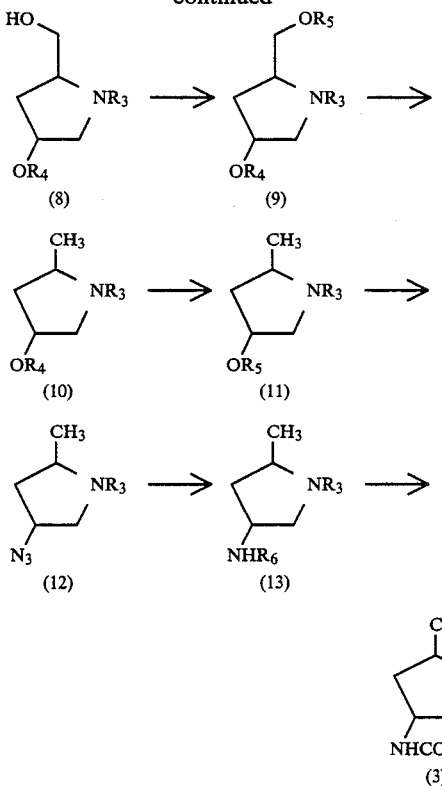

THF at a temperature of about 25° C. to obtain (10). Cleavage of the hydroxyl protecting group in (10) using an acid such as hydrofluoric acid, hydrobromic acid or hydrochloric acid or a base such as sodium hydroxide in aqueous THF or a source of fluoride ion such as cesium fluoride, potassium fluoride or preferably tetra-n-butylammonium fluoride in the preferential case where $R_5={}^tBuSi(CH_3)_2$-in a solvent such as THF, methanol or acetonitrile gives the alcohol (11) ($R_5=H$). Activation of the hydroxyl group in (11) by conversion to a leaving group such as p-toluenesulfonyloxy, trifluoromethanesulfonyloxy or preferably methanesulfonyloxy by treatment with methanesulfonyl chloride in the presence of a base such as triethylamine or pyridine in a solvent such as dichloromethane or THF at a temperature of about 0° C. to 40° C. furnishes (11) ($R=SO_2CH_3$). Displacement of the leaving group in (11) with a source of azide such as lithium azide, sodium azide or preferably tetra-n-butylammonium azide in a solvent such as acetonitrile at a temperature of about 30° C. to 80° C. gives (12). Reduction of the azide group with a hydride reagent such as lithium borohydride or sodium borohydride or preferably with hydrogen in the presence of a suitable catalyst in a solvent such as methanol at a temperature of about 25° C. affords the corresponding amine (13) ($R_6=H$) which is acetylated with acetic anhydride in the presence of a base such as triethylamine in a solvent such as pyridine or dichloromethane at a temperature of about $-15°$ C. to 40° C. to afford the N-acetylderivative (13) ($R_6=-COCH_3$). Alternatively, (12) can be converted directly to (13) ($R_6=-COCH_3$) upon treatment with thiolacetic acid. The nitrogen-protecting group $R_3$ is removed to give (13). In the preferable case where $R_3=COO^tBu$, this transformation is accomplished by treatment of (13) with an acid, preferably trifluoroacetic acid at temperature of about $-20°$ C. to 40° C. Compound (13) may be isolated as its trifluoroacetic acid salt, or alternatively the salt may be dissolved in a solvent such as methanol or dichloromethane and treated with a basic exchange resin. Filtration of the resin followed by concentration of the filtrate affords the base (13). Alternatively, compound (11) ($R_5=H$) may be transformed to (13) ($R_6=H$) by the method shown below.

The known hydroxyproline (6) ($R_2=R_3=H$) is first converted to its corresponding alkyl, aryl or arylalkyl ester, preferably its methylester, upon refluxing in methanol containing HCL. The ester (6) ($R_2=CH_3, R_3=H$) may be isolated as its hydrochloride salt. Protection of the amine function by conversion to a suitable carbamate or amide derivative, preferably using the tert-butoxycarbonyl group by treatment of (6) ($R_2=CH_3, R_3=H$) with di tert-butyl dicarbonate in the presence of a base such a triethylamine in a solvent such as dichloromethane or THF provides at a temperature of about $-10°$ C. to 25° C. (6) ($R_2=CH_3, R_3=-COO^tBu$). Protection of the secondary hydroxyl group with a suitable alkyl, alkoxyalkyl or silyl ether, preferably the tert-butyldimethylsilyl group by treatment of (6) ($R_2=CH_3, -COO^tBu$) with tert-butylchlorodimethylsilane in the presence of a base such as imidazole, triethylamine or pyridine in a suitable solvent such as dichloromethane, THF or N,N-dimethylformamide (DMF) at a temperature of about 0° C. to 60° C. furnishes compound (7) ($R_2=CH_3, -COO^tBu, {}^tBuSi(CH_3)_2$). The ester group in (7) is reduced with an appropriate hydride reagent such as lithium borohydride in a solvent such as THF or dimethoxyethane at a temperature of about $-20°$ C. to 25° C. to afford the corresponding primary alcohol (8). The primary alcohol in (8) is converted to a good leaving group such as p-toluenesulfonyloxy, trifluoromethanesulfonyloxy or preferably methanesulfonyloxy upon treatment with methanesulfonyl chloride in the presence of a base such as triethylamine in a solvent such as THF or preferably dichloromethane at a temperature of about $-10°$ C. to 30° C. to obtain (9) ($R_5=SO_2CH_3$). Deoxygenation of (9) is accomplished by treatment with a good source of nucleophilic hydride, preferably lithium triethylborohydride, in a solvent such as DMF or preferably

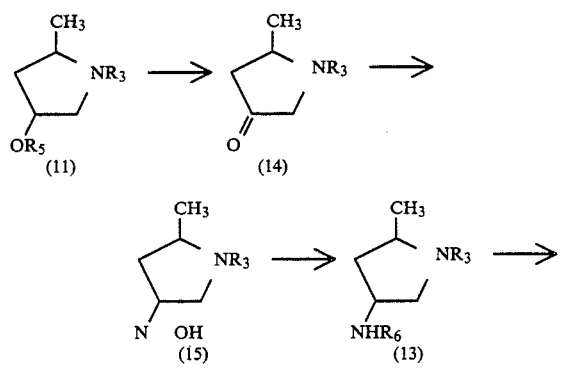

Oxidation of (11) ($R_5=H$), preferably employing the Swern protocol (DMSO,(ClCO)$_2$,CH$_2$Cl$_2$;Et$_3$N) provides the ketone (14). Treatment of (14) with hydroxylamine provides the corresponding oxime (15) which is reduced by hydrogen in the presence of a suitable catalyst such as Raney Nickel in a solvent such as methanol to afford the amine (13) ($R_6=H$).

The quinoline compounds according to this invention can be prepared by the reaction sequence illustrated below:

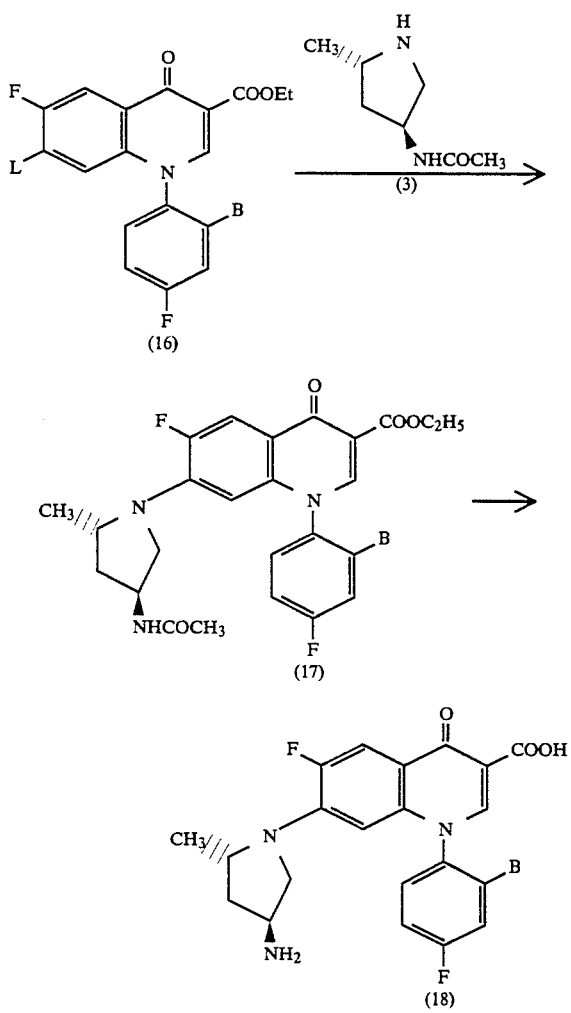

wherein B is hydrogen or fluoro and L is Cl or F.

Heating a compound (16) with an amine of compound (3) at a temperature of from 20° C. to 150° C., in the presence of a suitable organic polar or non-polar solvent such as dimethylsulfoxide, sulfolane, dimethylformamide (DMF), dimethylacetamide, 1-methy-2-pyrrolidinone, pyridine, water, tetrahydrofuran (THF) or methylene chloride provides compound (17). It is desirable to carry out the reaction in the presence of an acid-acceptor such as triethylamine, potassium carbonate or the like at a molar ratio of 1.0 to 2.0 moles of the acid-acceptor per mole of the compound (16). The amine (3) can also be used as acid acceptor in which 2 or more molar excess of this reagent is used. The ester in (17) is hydrolyzed by treatment with dilute sodium hydroxide in aqueous THF. Subsequent hydrolysis of the N-acetyl- group with hydrochloric acid furnishes the quinoline (18) ($R_1$ =H). The compounds (16) may be prepared in accordance with the prior art (D. Chu et al., Journal of Medicinal Chemistry, 1985, Vol. 28, 1558; D. Chu et al. 26th Interscience Conference on Antimicrobial Agents and Chemotherapy, Sept. 28-Octobrt 1, 1986; New Orleans, LA, Abstract #428).

The foregoing may be better understood from the following examples, which are presented for purposes of illustration and are not intended to limit the scope of the inventive concepts. As used in the following examples, the references to compounds, such as (1), (2), (3), etc., and to substituents, such as R, $R_1$, $R_2$, etc., refer to the corresponding compounds and substituents in the foregoing reaction scheme and formulae.

EXAMPLE 1

(2S,4S)-4-Acetamido-2-methylpyrrolidine (a) In a 2l round-bottom flask was placed 400 mL of methanol, and the system was cooled in an ice bath. To the system at ice temperature was added 50.3g (45.6 mL, 0.64 mol) of acetyl chloride dropwise through an addition funnel, followed by the addition of 60 g (0.46 mol) of 4-hydroxyproline. The reaction mixture was heated at reflux under nitrogen for 8 h and cooled to room temperature. Ether was added to the system, and the resulting white precipitate ((2R)—(6)($R_2$=$CH_3$,$R_3$=H).HCL, 84g, quantitative yield) was collected by suction filtration, mp 121–123° C.

(b) In a 2l round-bottom flask were placed 98 g (0.54 mol) of (2R,4R)—(6)($R_2$=$CH_3$,$R_3$=H).HCL and 650 mL of dichloromethane. To this suspension was added 164 g (220 mL, 1.72 mol) of triethylamine, and the system was immersed in an ice-salt bath. To the system was added 130 g (0.59 mol) of di-tert-butyl dicarbonate, and the reaction mixture was stirred under nitrogen for 12h, during which time the ice bath expired. The reaction mixture was washed with 1M aqueous phosphoric acid and saturated aqueous sodium bicarbonate, dried ($Na_2SO_4$) and concentrated with a rotary evaporator. The resulting yellow oil was crystallized from hexanes to obtain 118 g (90% yield) of pure (2R,4R)—(6)($R_2$=$CH_3$,$R_3$=—COO$^t$Bu) as a white solid, mp 74–77° C.

(c) In a 2l round bottom flask were placed 118 g (0.48 mol) of (2R,4R)-(6)($R_2$=$CH_3$,$R_3$=—COO$^t$Bu) and 150 mL of DMF. To this stirring solution were added 68.1 (1.0 mol)of imidazole and 80.1 g (0.53 mol) of tert-butylchlorodimethylsilane. The reaction mixture was stirred at room temperature under nitrogen for 1.5 h, diluted with ether and washed with water, 1M aqueous phosphoric acid and saturated aqueous sodium bicarbonate. The ether solution was dried ($Na_2SO_4$) and concentrated with a rotary evaporator to obtain 172 g (99% yield) of (2R,4R)—(7)($R_2$=$CH_3$,$R_3$=—COO$^t$Bu, $R_4$=—Si—$^t$Bu($CH_3$)$_2$) as a clear colorless oil.

(d) In a 3l 3-neck round-bottom flask were placed 169 g (0.47 mol) of (2R,4R)—(7)($R_2$=$CH_3$,$R_3$=—COO$^t$Bu,$R_4$=—Si—$^t$Bu ($CH_3$)$_2$) and 300 mL of THF. The system was placed under a nitrogen atmosphere and cooled in an ice-salt bath. To this stirring solution was added 15.6 g (0.72 mol) of lithium borohydride in 150 mL of THF dropwise through an addition funnel. The reaction mixture was stirred for 16h, during which time the ice bath expired. The reaction mixture was diluted with ethyl acetate, and ice was added to the system. After the ice melted, the layers were separated. To the organic phase was cautiously (exothermic) added 1M aqueous phosphoric acid. The layers were separated, and the organic phase was washed with saturated aqueous sodium bicarbonate and brine, dried ($Na_2SO_4$) and concentrated with a rotary evaporator to afford 146 g (93% yield) of (2R,4R)—(8)($R_3$=—COO$^t$-Bu,$R_4$=—Si$^t$Bu($CH_3$)$_2$) as a clear colorless oil.

(e) In a 1 liter round-bottom flask were placed 140 g (0.42 mmol) of (2R,4R)—(8)($R_3$=—COO$^t$Bu,$R_4$=—Si$^t$Bu(CH$_3$)$_2$) and 130 mL of dichloromethane. To the system was added 85.4 g (118 mL, 0.85 mol) of triethylamine. The system was cooled in an ice-salt bath, and 72.6 g (50 mL, 0.63 mol) of methanesulfonyl chloride was added to the mixture through an addition funnel. The reaction mixture was stirred under nitrogen for 15h, during which time the ice bath expired. The reaction mixture was partitioned between ethyl acetate and water. The ethyl acetate solution was washed with 1M aqueous phosphoric acid and saturated aqueous sodium bicarbonate, dried (Na$_2$SO$_4$) and concentrated with a rotary evaporator to obtain 162 g (94 g yield) of (2R,4R)—(9)($R_3$=—COO$^t$Bu,$R_4$=—Si—$^t$-Bu,(CH$_3$)$_2$$R_5$=—SO$_2$CH$_3$) as a viscous yellow oil.

(f) Under a nitrogen atmosphere, in a 3 liter 3-neck round-bottom flask were placed 80 g (0.20 mol) of (2R,4R)—(9)($R_3$=—COO$^t$Bu,$R_4$=—Si—$^t$-Bu(CH$_3$)$_2$,$R_5$=—SO$_2$CH$_3$) and 120 mL of THF. The system was cooled in an ice bath and 800 mL (0.80 mol) of 1M lithium triethylborohydride in THF was added to the system through an addition funnel. The cold bath was removed, and the reaction mixture was stirred at room temperature for 2 h. The mixture was diluted with ethyl acetate and washed with water, 1M aqueous phosphoric acid, saturated aqueous sodium bicarbonate and brine. The ethyl acetate solution was dried (Na$_2$SO$_4$) and concentrated with a rotary evaporator. The resulting oil was diluted with ethyl acetate, solids were removed by suction filtration and the filtrate was concentrated to obtain 59 g of clear yellow oil. This procedure was repeated on the same scale to afford 64 g of additional product. The crude material was combined and used without further purification. The oil from above was placed in a 1 liter round-bottom flask. To the system was added 430 mL (0.43 mol) of 1M tetra-n-butylammonium fluoride in THF. This solution was stirred under nitrogen for 2.5 h, diluted with 800 mL of ethyl acetate and washed with three 300 mL portions of water. The combined aqueous washings were extracted with four 100 mL portions of ethyl acetate. The combined organic fractions were dried (Na$_2$SO$_4$) and concentrated with a rotary evaporator to afford 117 g of yellow oil. The crude product was purified by flush column chromatoqraphy using 1:2 ethyl acetate/hexanes as the eluant to obtain 49.6 g (63 g yield) of pure (2S,4R)—(11)($R_3$=—COO$^t$Bu,$R_5$=H) as a white solid, mp 75–78° C.

(g) In a 1 liter round-bottom flask were placed 18.3 g (91 mmol) of (2S,4R)—(11)($R_3$=—COO$^t$Bu,$R_4$=H), 30 mL of dichloromethane and 23 g (32 mL, 0.23 mol) of triethylamine. The system was cooled in an ice bath. To the system was slowly added 20.8 g (14.4 mL, 182 mmol) of methanesulfonyl chloride. The reaction mixture was stirred under nitrogen for approximately 14 h, during which time the ice bath expired. The reaction mixture was diluted with ether, washed with 1M aqueous phosphoric acid and saturated aqueous sodium bicarbonate, dried (Na$_2$SO$_4$) and concentrated with a rotary evaporator to obtain 24.1 g of light red oil. This material was subjected to flash column chromatography using 1:1 ethyl acetate/hexanes as the eluant to obtain 16.1 q of oil. This oil was placed in a 1 liter round-bottom flask and dissolved in 25 mL of acetonitrile. To this solution was added 18.1 g (63.5 mmol) of tetra-n-butylammonium azide, and the mixture was heated at 65° C. for 3h under nitrogen. The reaction mixture was diluted with ether, and the upper ether layer was washed with two 100 mL portions of saturated aqueous sodium bicarbonate and brine. The combined aqueous washings and initial lower layer were extracted with three 100 mL portions of ether. The combined organic fractions were dried (Na$_2$SO$_4$) and concentrated with a rotary evaporator.

The crude material was purified by flash column chromatography using 1:1 ethyl acetate/hexanes as the eluant to obtain 8.75g (43 % yield) of pure (2S,4S)—(12)-($R_3$=—COO$^t$Bu) as an oil. (h) A solution of 8.86 g (39.2 mmol) of (2S,4S)—(12)($R_3$=—COO$^t$Bu) in 250 mL of methanol containing 4.2g of 10% palladium on carbon was placed under 4 atm of hydrogen. After 1h, the catalyst was removed by filtration through celite and the filtrate was concentrated with a rotary evaporator. In a 500 mL round-bottom flask were placed the crude amine (2S,4S)—(13)($R_3$=—COO$^t$-Bu,$R_6$=H) and 13 mL of pyridine. To the system was added 8.0 g (11.1 mL, 79.5 mmol) of triethylamine, and the system was cooled in an ice bath. To the system was added 8.1 g (7.5 mL, 79.5 mmol) of acetic anhydride, and the solution was stirred for 19 h at room temperature under nitrogen. The reaction mixture was diluted with chloroform and washed with 10% aqueous hydrochloric acid, saturated aqueous sodium bicarbonate and brine. The chloroform solution was dried (Na$_2$SO$_4$) and concentrated with a rotary evaporator to obtain 7.47 g of (2S,4S)—(13)($R_3$=—COO$^t$Bu,$R_6$=—COCH$_3$) as a red/brown gummy solid which was used in subsequent transformations without further purification. The purified acetamide (pale yellow solid) melts at 107–110° C.

(i) In a 50 mL round-bottom flask were placed 3.1 g (13 mmol) of the crude (2S,4S)—(13)($R_3$=—COO$^t$Bu, $R_6$=—COCH$_3$) prepared in Example 1(h) and 15 g (10 mL, 130 mmol) of trifluoroacetic acid. The solution was stirred under nitrogen for 15 min. and concentrated with a rotary evaporator. The residue was dissolved in 75 of methanol. To this solution was added 30 g of Rexyn 201(OH) resin which had been rinsed with ethanol. The mixture was stirred under nitrogen for 15 min., and 10g of additional resin was added to the mixture. The resin was removed by filtration through celite, and the filtrate was concentrated with a rotary evaporator to obtain 2g of crude (2S,4S)—(3)- which was used immediately for Example 2.

EXAMPLE 2
(2′S,4′S)-7-(4′-Amino-2′-methylpyrrolidin-1′-yl)-1-(o,p-difluorophenyl)-1,4-dihydro-6-fluoro-4-oxo-1,8-naphthyridine-3-Carboxylic Acid (a) In a 100 mL round-bottom flask were placed the crude (2′S 4′S)—(3) prepared in Example 1(i) and 6 mL of pyridine. To the system were added 1.4 g (2 mL, 13.9 mmol) of triethylamine and 5.5 g (14 mmol) of (2) (x=Cl,R=o,p-difluorophenyl,$R_1$=—CH$_2$CH$_3$. The reaction mixture was heated at 65° C. for 14 h under nitrogen, and the solvent was removed with a rotary evaporator. The crude material was purified by flash column chromatography to obtain 4.9 g (78 g yield) of (2′S,4′S)-(4)(R=o,p-difluorophenyl, $R_1$=—CH$_2$CH$_3$).

(b) In a 1 liter round-bottom flask were placed 4.9 g (10 mmol) of (2′S,4′S)-4(R=o,p-difluorophenyl, $R_1$=—CH$_2$CH$_3$) and 60 mL of THF. To the system was added 200 mL (20 mmol) of 0.1M aqueous sodium hydroxide, and the reaction mixture was heated at 65° C. for 3 h and was concentrated. The reaction mixture was concentrated with a rotary evaporator. To the system was added 400 mL of 6M aqueous hydrochloric acid, and the reaction mixture was heated at 110° C. for 15 h under nitrogen. The reaction mixture was concentrated with a rotary evaporator, and the solid residue was dissolved in approximately 200 mL of water. This solution was brought of pH 7 with saturated aqueous sodium bicarbonate, and the resulting precipitate was collected by suction filtration, rinsed with water, ethanol and ether and dried in a vacuum oven at 40° C. to obtain 2.65 g (63% yield) of (2'S,4'S)-(5)(R=o,p-difluorophenyl,$R_1$=H) as a white solid, mp 231–234° C. 1R (KBr): 1730, 1630cm$^{-1}$,$^1$HNMR (DMSO-d$_6$): delta 0.90 (broad m,3H), 1.67 (m,2H), 3.5 (broad m,4H), 7.33 (m,1H), 7.61 (m,1H), 7.80 (m,1H), 8.04 (d,1H,J=14), 8.79, 8.81 (2s,1H). Anal. Calc'd. for $C_{20}H_{17}F_3N_4O_3 \cdot 1/4H_2O$: C,56.80;H,4.177;N,13.25. Found: C,56.76;H,4.10,N,13.34.

EXAMPLE 3

Sulfuric Acid Salt of (2'S,4'S)-7-(4'-Amino-2'methylpyrrolidin-1'-yl)-1-(o,p-difluorophenyl)-1,4-dihydro-6-fluoro-4-oxo-1,8-naphthyridine-3-Carboxylic Acid Compound (2'S,4'S)—(5)(R=o,p-difluorophenyl, $R_1$=H) was prepared as described in Example 2. In an Erlenmeyer flask were placed 247 mg (0.591 mmol) of (2'S,4'S) (5)(R=o,p-difluorophenyl,$R_1$=H) and 1.48 mL (0.295 mmol) of 0.2M aqueous sulfuric acid. The mixture was heated, and 25 mL of water was added to the system. The solution was hot filtered, and the filtrate was freeze-dried to obtain 258 mg (93% yield) of (2'S,4'S) (5)(R=o,p-difluorophenyl,$R_1$=H)·½$H_2SO_4$ as a white solid, mp >260° C.

EXAMPLE 4

Hydrochloric Acid Salt of (2'S,4'S)-7-(4'-Amino-2'methylpyrrolidin-1'-yl)-1,4-dihydro-1-(o,p-difluorophenyl)-6-fluoro-4-oxo-1,8-naphthyridine-3-carboxylic acid Compound (2'S,4'S)-(5)(R=o,p-difluorophenyl, $R_1$=H) was prepared as described in Example 2. In an Erlenmeyer flask were placed 240 mg (0.574 mmol) of (2'S,4'S)-(5)(R=o,p-difluorophenyl,$R_1$=H) and 30 mL of 10 g aqueous hydrochloric acid, and the mixture was heated to boiling. The solution was concentrated with a rotary evaporator. The residue was dissolved in ethanol, and ether was added to this solution. The resulting precipitate was collected by suction filtration to afford 219 mg (84% yield) of (2'S,4'S)-(5)(R=o,p-difluorophenyl,$R_1$=H)·HCL as an off-white solid, mp >260° C.

EXAMPLE 5

Hydrochloric Acid Salt of (2'S,4'S)-7-(4Amino-2'-methylpyrrolidin-1'-yl) 1,4dihydro-6-fl 2'-1(p-fluorophenyl)4-oxo-1,8-naphthyridine-3-carboxylic acid (a) By replacing(2)(x=Cl,R=o,p-difluorophenyl, $R_1$=—CH$_2$CH$_3$) in Example 2a with (2) (x=Cl,R=p-fluorophenyl,$R_1$=—CH , one can obtain (2'S,4'S)-(4)(-R=p-fluorophenyl,$R_1$=—CHhd 2CH$_3$).

(b) By replacing (2'S,4'S)--(4)(R=o,p-difluorophenyl,$R_1$=—CH$_2$CH$_3$) in Example 2b with (2'S,440 S)—(4)(R=p-fluorophenyl,R$_1$=—CH$_2$CH$_3$) obtained in Example 2a, and replacing the neutralization portion of Example 2b with a recrystallization from 10% aqueous hydrochloric acid, one can obtain (2'S,4'S)—(5)(R=p-fluorophenyl,$R_1$=H)·HCL as a white solid. 1R (KBr): 1720, 1630 cm$^{-1}$ $^1$HNMR (DMSO-d$_6$): delta 0.98 (broad m,3H), 1.93 (m, 1H), 2,18 (m,1H), 3.5–3.9 (m,4H), 7.43 (dd,2H, J=9,9), 7.70 (dd, 2H,J=6,9), 8.15 (d,1H,J=14), 8.38 (broad, 2H), 8.68 (s,1H).

EXAMPLE 6

2'S,4'S)-7-(4'-Amino-2'-methylpyrrolidin-1'-yl)-1-(2,4-difluorophenyl)-1,4-dihydro-6-fluoro-4-oxo-quinoline-3-Carboxylic Acid (a) In a round-bottom flask was placed 0.78 g 3.2 mmol) of (2S,4S)-4-acetamido-1-tert-butoxycarbonyl-2-methylpyrrolidine To the system, at 0° C., was added 5 mL of trifluoroacetic acid. The cold bath was removed, and the solution was stirred at room temperature for 0.5 hour and concentrated with a rotary evaporator. The resulting oil was dissolved in 20 mL of methanol, and 3.8g of Rexyn 201 resin was added to the system. The mixture was stirred at room temperature for approximately 4 hours. During this period, an additional 3–4g of resin was added to the system. The mixture was filtered through a celite pad, and the filtrate was concentrated with a rotary evaporator to obtain a pale yellow oil. This material was used without further purification.

(b) Under a nitrogen atmosphere, in a 25 mL round-bottom flask were placed the 2S,4S)-4-acetamido-2-methylpyrrolidine obtained in part (a) and 1.5 mL of pyridine. To the system were added 1.28 g (3.5 mmol) of ethyl 6,7-difluoro-1-(2,4-difluorophenyl)4-dihydro-4-oxo-quinoline-3-carboxylate and 0.49 mL (353 mg, 3.5 mmol) of triethylamine. The reaction mixture was heated at 65° C. for 2 days and concentrated with a rotary evaporator. The crude material was subjected to flash column chromatography to obtain 1.03 g of (2'S,4'S)-ethyl 7-(4'-amino-2'-methylpyrrolidin1'-yl)-1-(2,4-difluorophenyl)-1,4-dihydro-6-fluoro-4-oxo-quinoline-3-carboxylic acid as a light yellow viscous oil which partially solidified under vacuum.

(c) Under a nitrogen atmosphere, in a 250 mL round-bottom flask were placed 1.02 g (2.09 mmol) of the material obtained in part (b) and 16 mL of THF. To the system was added 34.0 mL (3.4 mmol) of 0.1 M aqueous sodium hydroxide, and the solution was heated at 75° C. for approximately 0.5 hour. The reaction mixture was concentrated with a rotary evaporator. To the system was added 42 mL of 6 M aqueous hydrochloric acid, and the reaction mixture was heated under nitrogen at 110° C. for 12–13 hours. The temperature of the heating bath was increased to 118° C., 5 mL of 12 M aqueous hydrochloric acid was added to the system and the solution was heated for 2 hours. The reaction mixture was concentrated with a rotary evaporator, and the resulting yellow solid was dissolved in 1 M aqueous sodium hydroxide and extracted with several portions of chloroform. The aqueous solution was brought to pH7, and the resulting solid was collected by suction filtration. The solid was suspended in approximately 5 mL of ethanol, and the mixture was heated to boiling. The mixture was cooled in an ice batch, and the 2'S,4'S)-7-(4'-amino-2'-methylpyrrolidin-1'-yl)-l2,4-difluorophenyl)-1,4-dihydro-6-fluoro-4-oxo-quinolinecarboxylic acid (268 mg) was isolated as an off-white solid, mp 206–210° C. 1H NMR (DMSO-d ): delta 0.99, 1.02 (2 overlapping d, 3H, J=6),1.70 (m, 1H), 1.83 (m, 1H), 2.84–4.04 (complex, 4 H), 5. 86 (m, 1H), 7.44 (m, 1H). 7.75 (m, IH), 7.88 (d. 1H. J=15). 7.96 (m. 1H) 8.73, 8.77 (2s. 1H).

IN VITRO STUDIES

The in vitro antibacterial activity of the test compound was determined by conventional agar dilution procedures. The organisms were grown overnight in brain-heart infusion (BHI) broth (Difco 0037-01-6) at 36° C. Twofold dilutions of the stock solution (2000 g/mL) of the test compound were made in BHI agar obtain a test concentration ranging from 200 to 0.005 g/mL. The plate was inoculated with approximately $10^4$ organisms. It was then incubated at 36° C. for 18 h. the minimal inhibitory concentration was the lowest concentration of the test compound that yielded no visible growth on the plate.

The results of in vitro testing are shown in Tables 1 and 2 below.

TABLE 1

In Vitro Data - Naphthyridines

| ORGANISM | | MIC (MCG/ML) | |
|---|---|---|---|
| | | Example 2 | Example A* |
| P. aeruginosa | CFS 350F | 0.5 | 0.5 |
| P. aeruginosa | CMX 719A | 2 | 2 |
| P. aeruginosa | A 5005 | 0.5 | 0.5 |
| H. influenza | 504 | 0.008 | 0.15 |
| H. influenza | 519A | 0.008 | 0.15 |
| H. influenza | 566A | 0.008 | 0.15 |
| H. influenza | 588A | 0.008 | 0.008 |
| N. gonorrhoeae | CMX 591 | 0.06 | 0.06 |
| N. gonorrhoeae | 35F AMPI | 0.004 | 0.004 |
| L. pneumophila | ATCC 33152 | 0.25 | 0.25 |
| L. pneumophila | PHILA 2 | 0.25 | 0.25 |
| L. bozemanni | ATCC 33217 | 0.25 | 0.5 |
| B. fragilis | AT25285 | 0.5 | 0.4 |
| B. fragilis | UC-2 | 0.5 | 0.8 |
| C. difficile | ATCC 9689 | 1 | 1.6 |
| C. difficile | ATCC 17857 | 1 | 0.8 |

*7-(3-Amino-pyrrolidin-1-yl)-1-(2,4-difluorophenyl)-1,4-dihydro-6-fluoro-4-oxo-1,8-naphthyridine-3-carboxylic acid

TABLE 2

In Vitro Data - Quinolines

| | | MIC (MCG/ML) | |
|---|---|---|---|
| | | Ex. B* | Ex. 6 |
| STAPHYLOCOCCUS AUREUS | ATCC 6538P | .02 | .02 |
| STAPHYLOCOCCUS AUREUS | CMX 6868 | .05 | .05 |
| STAPHYLOCOCCUS AUREUS | A5177 | .05 | .2 |
| STAPHYLOCOCCUS AUREUS | 45 | .1 | .1 |
| STAPHYLOCOCCUS AUREUS | 45RAR2 | .1 | .1 |
| STAPHYLOCOCCUS AUREUS | CMX 503A | .05 | .1 |
| STAPHYLOCOCCUS AUREUS | CMX 553 | .05 | .1 |
| STAPHYLOCOCCUS EPIDERMIDIS | 3519 | .1 | .2 |
| MICROCOCCUS LUTEUS | ATCC 9341 | .39 | .2 |
| MICROCOCCUS LUTEUS | ATCC 4698 | .78 | .1 |
| ENTEROCOCCUS FAECIUM | ATCC 8043 | .2 | .1 |
| STREPTOCOCCUS BOVIS | A5196 | .39 | .2 |
| STREPTOCOCCUS AGALACTIRE | CMX 508 | .2 | .1 |
| STREPTOCOCCUS PYOGENES | EE561 | .2 | .2 |
| STREPTOCOCCUS PYOGENES | 930 CONST | .1 | .2 |
| ESCHERICHIA COLI | JUHL | 0.02 | 0.05 |
| ESCHERICHIA COLI | SS | .002 | < = .002 |
| ESCHERICHIA COLI | DC-2 | .2 | .2 |
| ESCHERICHIA COLI | H560 | .02 | .2 |
| ESCHERICHIA COLI | KNK 437 | .2 | .2 |
| KLEBSIELLA PNEUMONIAE | ATCC 8045 | .01 | .02 |
| PROVIDENCIA STUARTII | CMX 640 | 1.56 | 1.56 |
| PSEUDOMONAS AERUGINOSA | BMH10 | .1 | .78 |
| PSEUDOMONAS AERUGINOSA | A5007 | .2 | 3.1 |
| PSEUDOMONAS AERUGINOSA | K799/WT | .2 | .39 |
| PSEUDOMONAS AERUGINOSA | K799/61 | .05 | .02 |
| PSEUDOMONAS CEPACIA | 296I | 6.2 | 12.5 |
| ACINETOBACTER SP | CMX 669 | .05 | .1 |

*7-(3-Amino-pyrrolidin-1-yl)-1-(2,4-difluorophenyl)-1,4-dihydro-6-fluoro-4-oxo-quinoline-3-carboxylic acid In Vitro Data - Naphthyridines

| ORGANISM | | MIC (MCG/ML) | |
|---|---|---|---|
| | | Example 2 | Example A* |
| S. aureus | CMX 730A | 0.03 | 0.03 |
| S. aureus | CMX 705 | 0.03 | 0.03 |
| S. aureus | ATCC 25923 | 0.06 | 0.03 |
| S. aureus | GYR 1162 | 0.03 | 0.03 |
| E. faecalis | CMX 729G | 0.25 | 0.25 |
| E. faecalis | GYR 1166 | 0.5 | 0.5 |
| S. agalactiae | CMX 508 | 0.12 | 0.12 |
| S. pyogenes | M79061-98 | 0.25 | 0.25 |
| E. coli | ATCC 25922 | 0.03 | 0.03 |
| E. coli | CMX 733 | 0.03 | 0.03 |
| E. coli | CMX 756 | 0.03 | 0.03 |
| E. coli | CMX 744A | 0.03 | 0.03 |
| K. pneumoniae | CMX 724A | 0.06 | 0.06 |
| K. pneumoniae | CMX 735A | 0.06 | 0.06 |
| P. mirabilis | CMX 704F | 0.25 | 0.25 |
| P. mirabilis | CMX 729B | 0.25 | 0.12 |
| P. aeruginosa | CFS 387C | 0.5 | 1 |

SOLUBILITY STUDIES

A known excess weight of the compound was shaken overnight with a known volume of Ringer's buffer (bicarbonate buffer containing sodium, potassium, calcium and magnesium ions, initially adjusted to pH 7.5). The contents were filtered, and the clear filtrate was analyzed after appropriate dilution using HPLC (UV absorbance detection). The results of such solubility analysis is shown in Table 3.

TABLE 3

AQUEOUS SOLUBILITY
(at pH 7.5 in Ringer's buffer)

| COMPOUND | SOLUBILITY (MG/ML) |
|---|---|
| Example A | 0.008 |

TABLE 3-continued

| AQUEOUS SOLUBILITY (at pH 7.5 in Ringer's buffer) | |
|---|---|
| COMPOUND | SOLUBILITY (MG/ML) |
| Example 2 | 0.15 |
| Epimer of Example 2 | 0.34 |
| Example B | 0.008 |
| Example 6 | 0.053 |
| Epimer of Example 6 | 0.182 |

The solubility data shown in Table 3 indicates that compounds 2 and 6 show significantly improved aqueous solubility properties compared with their respective 2-unsubstituted aminopyrrolidine analogs A and B.

PHARMACOKINETIC STUDIES

Mice were administered the quantity of compound indicated orally, as a single dose. At the specified time intervals, blood was collected from groups of five mice. All samples were assayed by a disk agar diffusion bioassay procedure. *Bacillus subtilis* 6633 or *Klebsiella pneumoniae* 10032 were used as the assay organisms, and seek agar medium No. 1 (BBL Microbiology Systems; Cockeysville, MD) was the growth medium. The plates were incubated at 32° C for 18 h and read with an image analyzer (Optomax Inc.). The results of such pharmacokinetic analysis are shown in Table 4.

TABLE 4

| COMPARATIVE PHARMACOKINETIC DATA | | | | | | | |
|---|---|---|---|---|---|---|---|
| | Oral Dose* | Blood Level of Compound (ug/ml) t(h) | | | | | |
| Compound | (mg/kg) | 0.5 | 1.0 | 2.0 | 3.0 | 6.0 | 24.0 |
| Example 2 | 25 | 5.9 | 3.2 | 3.3 | 2.8 | 1.3 | 0.2 |
| Example A | 100 | — | 2.3 | 1.7 | 1.7 | 0.9 | — |
| Example 6 | 25 | 3.7 | 4.3 | 2.8 | 1.1 | 0.1 | 0.0 |
| Example B | 100 | — | 0.5 | 0.7 | 0.9 | 0.7 | 0.0 |

*Please note that Examples A and B were administered at 4 times the dose of Examples 2 and 6, yet Examples 2 and 6 still achieve better blood levels than their respective 2-unsubstituted pyrrolidinyl derivatives.

The pharmacokinetic data shown in Table 4 indicates that compounds 2 and 6 have greatly improved oral absorption properties when compared with their respective 2-unsubstituted aminopyrrolidine analogs A and B. Compounds 2 and 6 achieve higher serum concentrations when administered orally at 25 mg/kg than their respective 2-unsubstituted analogs A and B achieve when administered at 100 mg/kg.

It will be understood that various changes and modifications can be made in the details of procedure, formulation and use without departing from the spirit of the invention, especially as defined in the following claims.

We claim:

1. A compound having the formula:

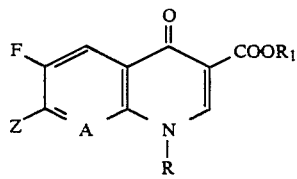

wherein A is CH or N; $R_1$ is hydrogen or a carboxy protecting group; R is selected from o,p-difluorophenyl or p-fluorophenyl; and z is (2S, 4S-4-amino-2-methyl-pyrrolidin-1yl; and pharmaceutically acceptable salts thereof.

2. A compound as defined in claim 1 wherein $R_1$ is hydrogen.

3. A compound as defined in claim 1 wherein R is o,p-difluorophenyl, Z is (2S,4S)-4-amino-2-methylpyrrolidin-1-yl and $R_1$ is hydrogen.

4. A compound as defined in claim 3 wherein A is N.

5. A compound as defined in claim 1 wherein R is p-fluorophenyl, Z is (2S,4S)-4amino-2-methylpyrrolidin-1-yl and $R_1$ is hydrogen.

6. The compound having the formula:

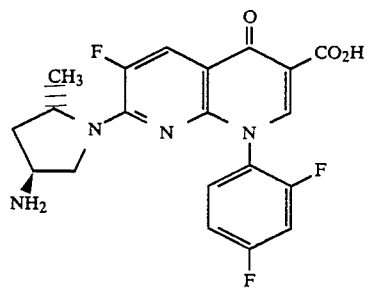

or pharmaceutically acceptable salts thereof.

7. A composition having antibacterial activity and improved solubility and pharmacokinetic profile in pharmaceutical dosage form containing a diluent and the compound as defined in claim 6.

8. A method of treating a bacterial infection in a patient comprising administering to a patient in need a therapeutically effective amount of the compound as defined in claim 6.

9. The compound having the formula;

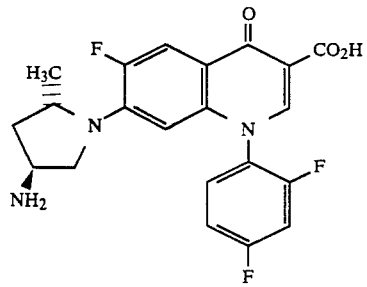

or pharmaceutically acceptable salts thereof.

10. A composition having antibacterial activity and improved solubility and pharmacokinetic profile in pharmaceutical dosage form containing a diluent and the compound as defined in claim 9.

11. A method of treating a bacterial infection in a patient comprising administering to a patient in need a therapeutically effective amount of the compound as defined in claim 9.

12. A composition having antibacterial activity and improved solubility and pharmacokinetic profile in pharmaceutical dosage form containing a diluent and a compound as defined in claim 1.

13. A method of treating a bacterial infection in a patient comprising administering to a patient in need a therapeutically effective amount of a compound as defined in claim 1.

* * * * *